(12) United States Patent
Parker et al.

(10) Patent No.: US 9,316,519 B2
(45) Date of Patent: Apr. 19, 2016

(54) SAMPLE CAPTURE ASSURANCE FOR SAMPLE BOTTLES

(71) Applicant: Schlumberger Technology Corporation, Sugar Land, TX (US)

(72) Inventors: Grant Parker, Sweeny, TX (US); Sridhar Sana, Katy, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 173 days.

(21) Appl. No.: 14/099,140

(22) Filed: Dec. 6, 2013

(65) Prior Publication Data
US 2015/0160061 A1 Jun. 11, 2015

(51) Int. Cl.
| | | |
|---|---|---|
| *E21B 47/00* | (2012.01) | |
| *G01F 17/00* | (2006.01) | |
| *E21B 49/08* | (2006.01) | |
| *G01N 1/20* | (2006.01) | |

(52) U.S. Cl.
CPC .............. *G01F 17/00* (2013.01); *E21B 49/081* (2013.01); *G01N 1/2035* (2013.01); *G01N 2001/2071* (2013.01)

(58) Field of Classification Search
None
See application file for complete search history.

(56) References Cited

U.S. PATENT DOCUMENTS

| | | | |
|---|---|---|---|
| 3,254,531 A | | 6/1966 | Briggs, Jr. |
| 5,318,130 A | | 6/1994 | Manke |
| 5,337,822 A | * | 8/1994 | Massie et al. ................. 166/264 |
| 6,058,773 A | | 5/2000 | Zimmerman et al. |
| 6,435,279 B1 | | 8/2002 | Howe et al. |
| 7,155,990 B2 | | 1/2007 | Gilbert |
| 2013/0276553 A1 | * | 10/2013 | Yushko ................. E21B 49/086 73/863.86 |
| 2014/0299383 A1 | * | 10/2014 | Tao ............................... 175/236 |
| 2014/0345860 A1 | * | 11/2014 | Van Zuilekom ...... E21B 49/081 166/264 |

FOREIGN PATENT DOCUMENTS

WO 2011011918 A1 2/2011

* cited by examiner

*Primary Examiner* — Andre Allen
(74) *Attorney, Agent, or Firm* — Kenneth L. Kincaid

(57) ABSTRACT

An arrangement for determining a state of a sample bottle, having an external housing, a fluid chamber configured to hold a fluid obtained from an environment, the fluid chamber within the external housing, a separation piston positioned at one end of the fluid chamber, the separation piston configured to move from a first position to a second position; a closure device configured to establish a closure; a protrusion extending from a central rod, the protrusion extending into a flowline; the central rod positioned within the external housing, the central rod configured to interface with the separation piston and move the separation piston from the first position to the second position and a limit switch located at a peripheral end of the protrusion, the limit switch configured to limit movement of the central rod when the limit switch is activated.

19 Claims, 4 Drawing Sheets

SAMPLE CAPTURE ASSURANCE FOR SAMPLE BOTTLES

CROSS-REFERENCE TO RELATED APPLICATIONS

None.

FIELD OF THE INVENTION

Aspects relate to downhole fluid analysis. More specifically, aspects relate to sample capture assurance for sample bottles in downhole fluid analysis systems.

BACKGROUND INFORMATION

Sample bottles are used to sample fluids from a downhole environment and transport those fluids to an uphole environment for testing and identification. Sample bottles are regularly used in typical oil field service work and are a vital component of technologies used in modern drilling operations.

Typical sample bottles have several drawbacks that may cause error during sampling. In these typical sample bottles, a separation piston is positioned and constructed so that the piston can slide in a fluid chamber and along a central rod. The position of the separation piston is used as an indicator of sample capture. The separation piston can have a relatively long stroke. By way of example, the typical stroke is approximately one (1) meter. If the detection of the stroke is performed with a precision of two (2) percent of the entire measurement range, this translates into an uncertainty of approximately two (2) centimeers on the piston position.

This uncertainty may be insufficient for the purpose of assuring that the bottle is full or properly sealed.

SUMMARY

The following summary is provided for an example embodiment. The summary provided is not to be considered limiting as to the possible implementations of the aspects described. In one embodiment, an arrangement for determining a state of a sample bottle, comprising: an external housing, a fluid chamber configured to hold a fluid obtained from an environment. the fluid chamber within the external housing, a separation piston positioned at one end of the fluid chamber, the separation piston configured to move from a first position to a second position, a closure device configured to establish a closure, a protrusion extending from a central rod, the protrusion extending into a flowline, the central rod positioned within the external housing, the central rod configured to interface with the separation piston and move the separation piston from the first position to the second position and a limit switch located at a peripheral end of the protrusion, the limit switch configured to limit movement of the central rod when the limit switch is activated.

DETAILED DESCRIPTION

The following embodiments provide a sample bottle to determine if the sample bottle has achieved a desired level of filling. In each embodiment, the sample bottle is placed in a downhole environment to sample fluid from a geological formation. Such embodiments are used in oil field services applications. In each configuration provided, the embodiments presented have superior sampling capabilities as an operator can determine if the sample bottle is fully charged. Three different embodiments for determining the sample bottle filling percentage are provided. A person of skill in the art will recognize that other alternatives within the scope of the aspects described are within the scope of disclosure.

In the embodiments, the sample bottles are used in either a while drilling embodiment of a drill string or on a wireline. Such bottles are used to sample fluids (both liquids, gases and mixtures of these materials) and bring those sample fluids back to the surface for analysis. Such bottles may be over one meter long or may be shorter, based upon the volumetric needs for analysis.

As the embodiments presented are important for ultimate analysis of the fluids that are contained therein, the materials that are used for construction are rugged materials, such as metals, that are made to withstand shock, vibration and temperature. Such metals may be corrosion resistant materials and the bottles may be insulated or have heaters to maintain the obtained samples at environmental conditions close to the conditions during sampling. The sample bottles described may be single units or may be arranged in banks of bottles to allow operators the ability to fill multiple containers. If the sample bottles are arranged in banks, the bottles may be connected in series or parallel, according to the needs of operators so that samples may be simultaneously obtained or obtained in a series relationship to one another.

Figure 1:
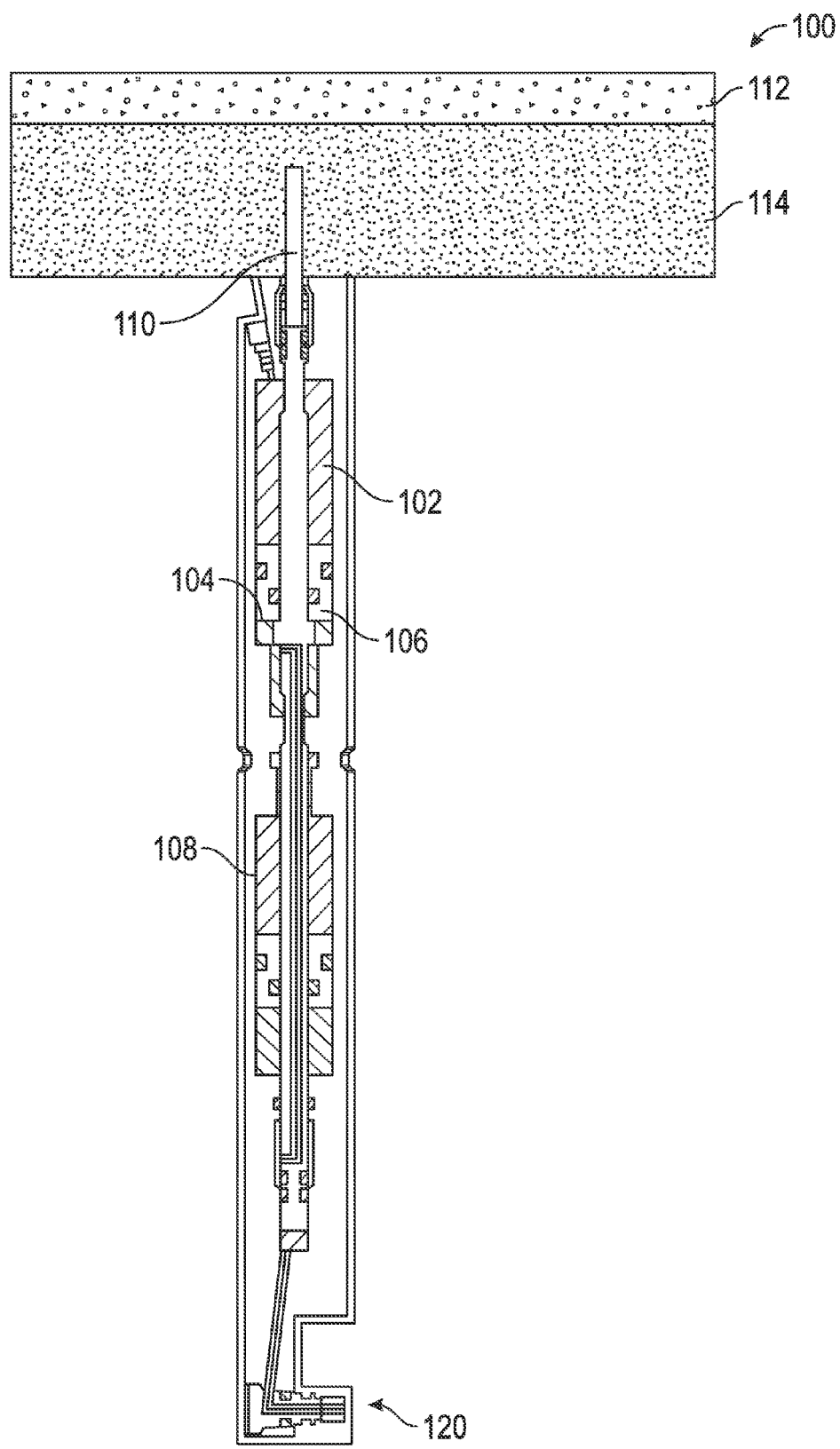
FIG. 1 is a side sectional view of a sample capture device in accordance with one example embodiment.

Referring to FIG. 1, a sample bottle 100 is illustrated. The sample bottle 100 has a fluid chamber 102, located at the top of the bottle 100. A closure device 104 allows the sample bottle 100 to be closed or opened at the desired direction of operators. The closure device 104 may be constructed from rugged materials to allow the sample bottle 100 to be operated multiple times without degradation to the sample bottle 100. A separation piston 106 separates the fluid chamber 102 from the remainder of the tool and creates at least one boundary for the fluid chamber 102. A central rod 108 controls the separation piston 106 position during the stroke of the separation piston 106. The central rod 108 may be controlled electrically, mechanically or fluidically, as necessary. In the embodiments described, both the separation piston 106 and the central rod 108 may be separately moved, at the discretion of the operator. In other non-limiting embodiments, the movement of the central rod 108 can be controlled by the operator and the separation piston 106 is connected to the central rod 108 such that the separation piston 106 is moved when the central rod 108 is moved. An exit port 120 is located at the base of the bottle 100 such that fluids may be injected or removed from the base of the bottle 100. The injection or removal of the fluids control the central rod 108, thereby actuating the separation piston 106 and the protrusion 110.

Figure 2:
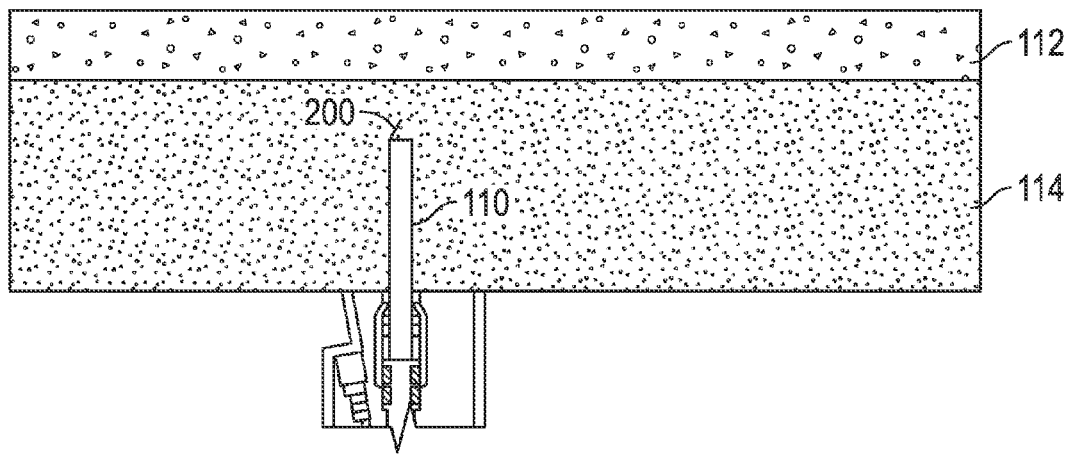
FIG. 2 is a side sectional view of the sample capture device limit switch arrangement of FIG. 1.

As provided in FIG. 2, a limit switch 200 located on a protrusion 110 controls and limits the progression of the separation piston 106 if the limit switch 200 is activated. The limit switch 200 is located at the top of the protrusion 110 and adjacent to the carrier 112 at the periphery of the flowline bus 114. The limit switch 200, upon contact with the carrier 112, may be tripped, thereby limiting further outward positional change of the central rod 108. In an alternative configuration, the limit switch 200 does not require contact with the carrier 112 for activation.

Figure 3:
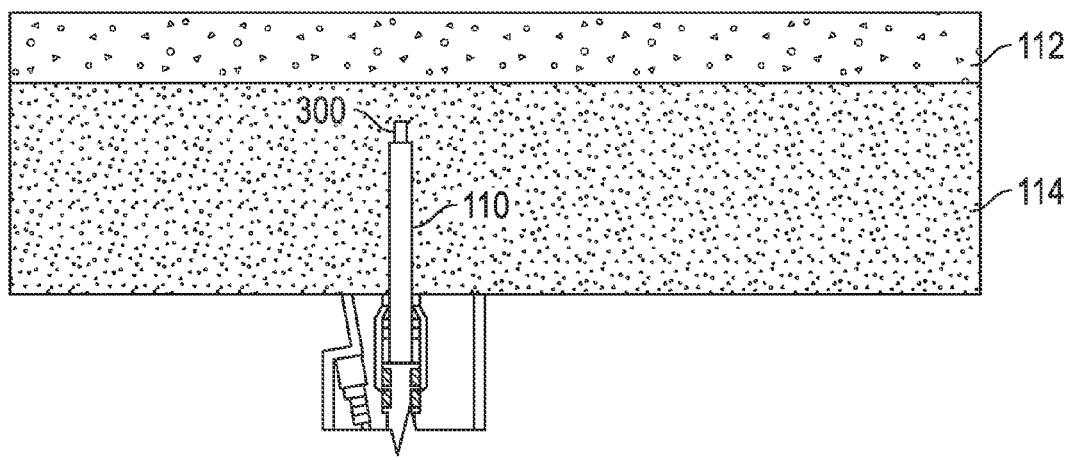
FIG. 3 is side sectional view of the sample capture device limit switch arrangement of FIG. 1 with a proximity sensor.

Referring to FIG. 3, in an alternative configuration, a proximity sensor 300 may be positioned at the top of the protrusion 110. The proximity sensor 300 may be positioned such that the proximity sensor 300 activates and limits movement of the central rod 108 upon achieving a specified position in relation to the carrier 112.

Figure 4:
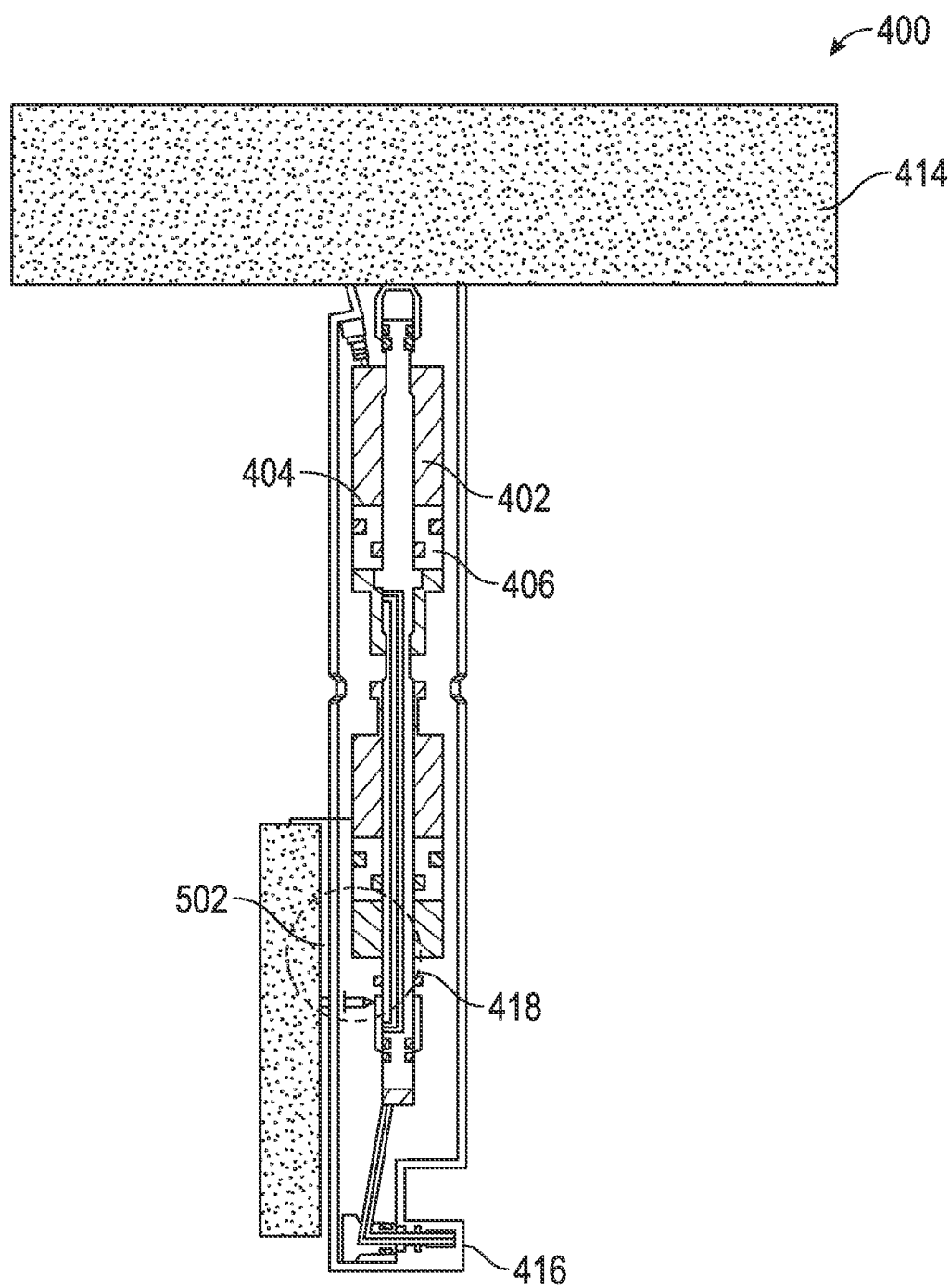
FIG. 4 is a side sectional view of an embodiment of a sample capture device with protrusion arrangement.

Referring to FIG. 4, a sample bottle 400 according to a different aspect is illustrated. The sample bottle 400 is configured to withdraw fluid from the flowline bus 414 illustrated at the top of the sample bottle 400. The sample bottle 400 has a separation piston 406 that separates a fluid chamber 402 from the remainder of the device. A closure device 404 is located, as illustrated, at the bottom of the separation piston 406. An exit port 416 is positioned at the bottom of the sample bottle 400. A protrusion arrangement 418 is provided such that a measurement may be made of the overall position of the separation piston 406 within the tool. Movement of the separation piston 406 will allow the sample bottle to remove fluid from the flowline bus 414.

Figure 5:
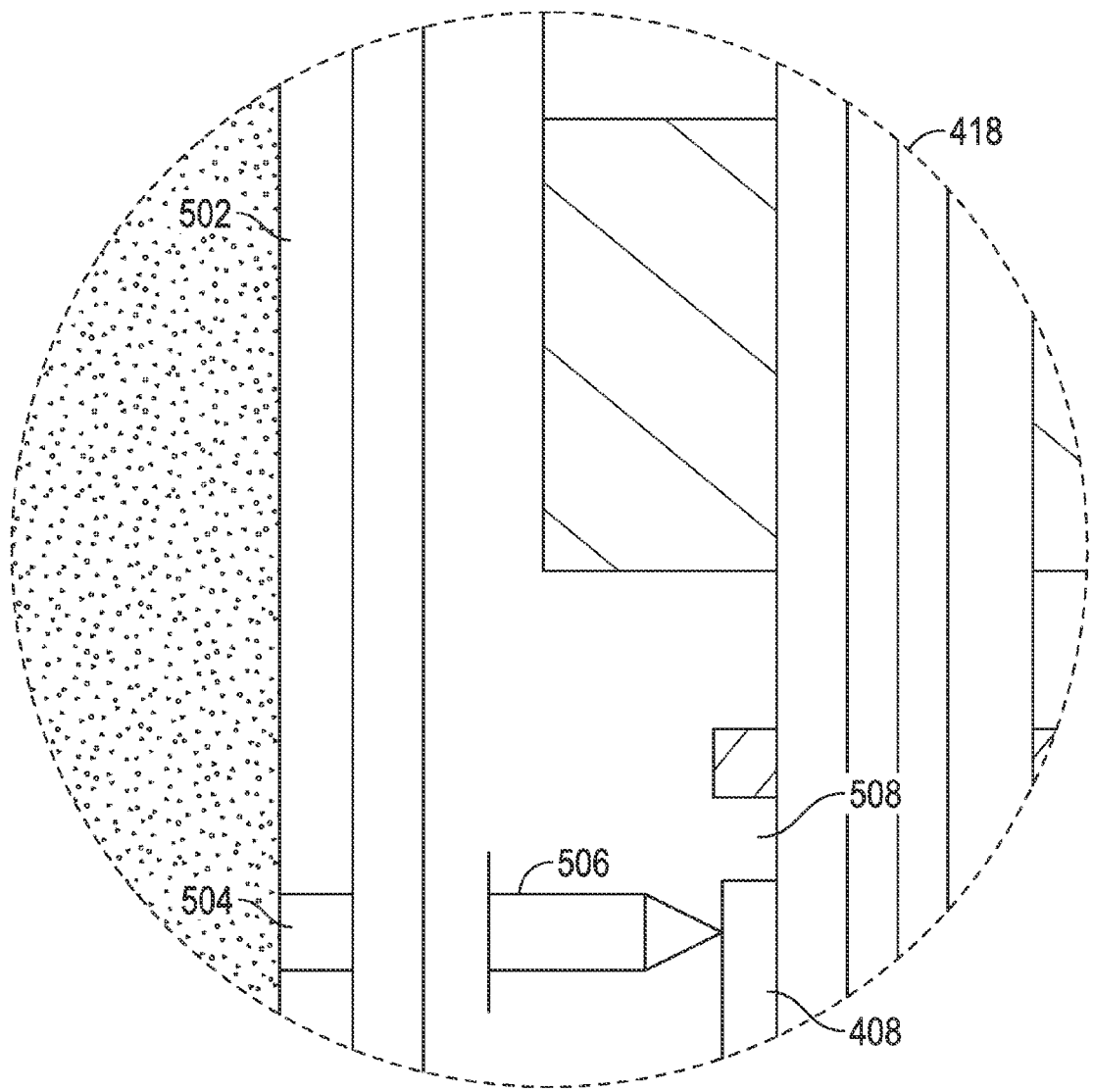
FIG. 5 is a side view of the protrusion arrangement of the sample capture device in FIG. 4.

Referring to FIG. 5, a close-up view of the protrusion arrangement 418 is illustrated. A separate carrier 502 has a proximity sensor 504 that is tuned to identify a position of the protrusion arrangement 418. In the illustrated embodiment, the proximity sensor 504 has a coil. The protrusion 506 has a magnet (or other ferromagnetic material) carried at the outermost end. Movement of the protrusion 506 into the adjacent notch 508 can be identified by the proximity sensor 504, thus identifying a full fluid chamber 402 as determined by the separation piston 406. The central rod 408 is used to control the separation piston 106 ultimate position. The central rod 408 may be hydraulically or mechanically actuated.

In the described aspects previously described, the protrusion can be made of a non-metallic material that is more transparent to a magnetic field than the metallic body of a sample bottle, therefore facilitating the implementation of detection sensor based on detection of a permanent magnet, for example a Hall effect sensor.

In a sample bottles described, the separation piston is constructed so that the separation piston can slide in a fluid chamber and along a central rod. Towards the end of the piston stroke, the piston engages a closure device of the rod and shifts the rod to a position in which the chamber volume is maximum, that is the sample bottle is full.

In conventional systems, the systems are insufficient in their accuracy levels to ensure that the sample bottle is full or properly sealed. In contrast, aspects described detect the position of a protrusion connected to the rod, which has a relatively short stroke. For example, the piston slides freely along the rod by 95% of its total stroke before engaging the closure device, and then shift the rod by the remaining 5% of its stroke.

By contrast, when the protrusion is measured with the same accuracy as that of conventional rods systems, the uncertainty of the measurement is now approximately one (1) millimeter, a much smaller distance than the one obtained previously with the measurement of piston position. This uncertainty level is more adequate for the purpose of assuring that a bottle is full or properly sealed.

In another alternative embodiment, the protrusion may be made of a nonmetallic material that is more transparent to magnetic fields than the metallic body of a sample bottle, therefore facilitating the implementation of detection sensors based on detection of a permanent magnet, for example a Hall effect sensor.

In one non-limiting embodiment, an arrangement for determining a state of a sample bottle is described comprising an external housing, a fluid chamber configured to hold a fluid obtained from an environment. the fluid chamber within the external housing, a separation piston positioned at one end of the fluid chamber, the separation piston configured to move from a first position to a second position, a closure device configured to establish a closure, a protrusion extending from a central rod, the protrusion extending into a flowline, the central rod positioned within the external housing, the central rod configured to interface with the separation piston and move the separation piston from the first position to the second position and a limit switch located at a peripheral end of the protrusion, the limit switch configured to limit movement of the central rod when the limit switch is activated.

In another non-limiting embodiment, the arrangement may further comprise a carrier, the carrier configured to interact with the limit switch.

In another non-limiting embodiment, the arrangement may further comprise an exit port located in the external housing.

In another non-limiting embodiment, an arrangement for determining a state of a sample bottle is provided comprising an external housing, a fluid chamber configured to hold a fluid obtained from an environment. the fluid chamber within the external housing, a separation piston positioned at one end of the fluid chamber, the separation piston configured to move from a first position to a second position, a closure device configured to establish a closure, a protrusion extending from a central rod, the protrusion extending into a flowline, the central rod positioned within the external housing, the central rod configured to interface with the separation piston and move the separation piston from the first position to the second position and a proximity sensor located at a peripheral end of the protrusion, the proximity sensor configured to limit movement of the central rod when the proximity sensor is activated.

In another non-limiting embodiment, the arrangement may further comprise a carrier, the carrier configured to interact with the proximity sensor.

In another non-limiting embodiment, the arrangement may further comprise an exit port located in the external housing.

In a still further embodiment, an arrangement for determining a state of a sample bottle, may comprise an external housing, a fluid chamber configured to hold a fluid obtained from an environment, the fluid chamber within the external housing, a separation piston positioned at one end of the fluid chamber, the separation piston configured to move from a first position to a second position, a closure device configured to establish a closure, a protrusion extending from a central rod, the protrusion extending into a flowline, the central rod positioned within the external housing, the central rod configured to interface with the separation piston and move the separation piston from the first position to the second position, a carrier configured to one of abut and be adjacent to the external housing and a proximity sensor located in the carrier, the proximity sensor configured to limit movement of the central rod when the proximity sensor is activated.

In another embodiment, the arrangement may be configured wherein the separation piston is configured to be actuated by one of mechanically and hydraulically.

In another embodiment, the arrangement may be configured wherein the separation piston is not independently moveable from the central rod.

In another embodiment, the arrangement may be configured wherein the external housing is configured to house the closure device, the separation piston, fluid chamber and the central rod.

In another embodiment, The arrangement according to claim 7 wherein the protrusion is configured with a coil.

While the aspects have been described with respect to a limited number of embodiments, those skilled in the art, having benefit of the disclosure, will appreciate that other embodiments can be devised which do not depart from the scope of the disclosure herein.

What is claimed is:

1. An arrangement for determining a state of a sample bottle, comprising:
   an external housing defining an interior space;
   a fluid chamber configured to hold a fluid obtained from an environment, the fluid chamber within the external housing and the interior space;
   a separation piston positioned at one end of the fluid chamber, the separation piston configured to move from a first position to a second position;
   a closure device configured to establish a closure of the fluid chamber;
   a central rod positioned within the external housing, the central rod configured to interface with the separation piston and move the separation piston from the first position to the second position;
   a protrusion extending from the central rod, the protrusion extending into a flowline; and
   a limit switch located at a peripheral end of the protrusion, the limit switch configured to limit movement of the central rod when the limit switch is activated.

2. The arrangement according to claim 1, further comprising:
   a carrier, the carrier configured to interact with the limit switch.

3. The arrangement according to claim 1, further comprising:
   an exit port located in the external housing.

4. An arrangement for determining a state of a sample bottle, comprising:
   an external housing;
   a fluid chamber configured to hold a fluid obtained from an environment. the fluid chamber within the external housing;
   a separation piston positioned at one end of the fluid chamber, the separation piston configured to move from a first position to a second position;
   a closure device configured to establish a closure;
   a central rod positioned within the external housing, the central rod configured to interface with the separation piston and move the separation piston from the first position to the second position;
   a protrusion extending from the central rod, the protrusion extending into a flowline; and
   a proximity sensor located at a peripheral end of the protrusion, the proximity sensor configured to limit movement of the central rod when the proximity sensor is activated.

5. The arrangement according to claim 4, further comprising:
   a carrier configured to interact with the proximity sensor.

6. The arrangement according to claim 4, further comprising:
   an exit port located in the external housing.

7. An arrangement for determining a state of a sample bottle, comprising:
   an external housing;
   a fluid chamber configured to hold a fluid obtained from an environment, the fluid chamber within the external housing;
   a separation piston positioned at one end of the fluid chamber, the separation piston configured to move from a first position to a second position;
   a closure device configured to establish a closure;
   a central rod positioned within the external housing, the central rod configured to interface with the separation piston and move the separation piston from the first position to the second position;
   a carrier configured to one of abut and be adjacent to the external housing; and
   a proximity sensor located in the carrier, the proximity sensor configured to limit movement of the central rod when the proximity sensor is activated.

8. The arrangement according to claim 1, wherein the separation piston is configured to be actuated by one of mechanically and hydraulically.

9. The arrangement according to claim 4, wherein the separation piston is configured to be actuated by one of mechanical and hydraulic interaction.

10. The arrangement according to claim 7, wherein the separation piston is configured to be actuated by one of mechanical and hydraulic interaction.

11. The arrangement according to claim 1, wherein the separation piston is not independently moveable from the central rod.

12. The arrangement according to claim 4, wherein the separation piston is not independently movable from the central rod.

13. The arrangement according to claim 7, wherein the separation piston is not independently movable from the central rod.

14. The arrangement according to claim 1, wherein the external housing is configured to house the closure device, the separation piston, fluid chamber and the central rod.

15. The arrangement according to claim 4, wherein the external housing is configured to house the closure device, the separation piston and central rod.

16. The arrangement according to claim 7, wherein the external housing is configured to house the closure device, the separation piston, fluid chamber and the central rod.

17. The arrangement according to claim 16, wherein the proximity sensor is configured with a coil.

18. The arrangement according to claim 7, comprising a protrusion disposed in the external housing, wherein the proximity sensor is configured to identify a position of the protrusion.

19. The arrangement according to claim 18, wherein the protrusion comprises a magnet or a ferromagnetic material.

* * * * *